United States Patent [19]

Smolko

[11] Patent Number: 4,867,181

[45] Date of Patent: Sep. 19, 1989

[54] NON-SMOKING AID

[76] Inventor: Milan S. Smolko, P.O. Box 20, Clarks Summit, Pa. 18411

[21] Appl. No.: 840,777

[22] Filed: Mar. 18, 1986

[51] Int. Cl.⁴ ............................................. A24F 47/00
[52] U.S. Cl. .................................... 131/270; 131/329
[58] Field of Search ........................ 131/270, 359, 329

[56] References Cited

FOREIGN PATENT DOCUMENTS 2747500  4/1979  Fed. Rep. of Germany ...... 131/270

Primary Examiner—V. Millin
Attorney, Agent, or Firm—Kane, Dasimer, Sullivan, Kurucz, Levy, Eisele and Richard

[57] ABSTRACT

An antismoking mouthwash to assist in reducing the smoking habit comprises a stabilized silver nitrate in aqueous solution. The aqueous solution is shelf stabilized with the presence of 0.001 to 0.005 weight percent of nitric acid and protection from exposure to light. The shelf stable solution of silver nitrate is used in a method of aiding in the reduction of the tobacco smoking habit, in a human afflicted with such a habit, by applying the shelf stable solution topically to the mucosa of the oral cavity of the afflicted human under a particular and prescribed application schedule.

9 Claims, No Drawings

NON-SMOKING AID

BACKGROUND OF THE INVENTION

1. Field of the Invention

The invention relates to a mouthwash to aid smokers attempting to quit the smoking habit.

2. Brief Description of the Prior Art

The undesirable effects and habituation of smoking tobacco has caused a desire in cigarette, cigar, and pipe smokers to quit their smoking habit. However withdrawal from nicotine addiction is difficult and the would be non-smoker often needs assistance.

Aids have been developed to assist the smoker in his dilemma and may be classified as either those which decrease anxiety during withdrawal and thus reduce the desire to the user for nicotine and the more recently developed aids which cause a physiological distaste for tobacco smoke.

Aids which reduce anxiety during nicotine withdrawal have excellent potential; however, at present they have shortcomings. For example, a chewing gum containing nicotine is useful in aiding smokers to quit smoking. But the gum is contraindicated during pregnancy or if the smoker has heart disease. Nicotine chewing gum (the only antismoking aid on the market in the USA) causes or aggravates: heat palpitations; heart attacks; arterial diseases (obliterating arteries); hypertension; peptic ulcer; diabetes; hyperthyrodism; oesophagits; sore throat; upset stomach; hiccups; nausea; mouth ulcers; addiction (dependence) to nicotine in 7-10% of users.

In the latest concept in anti-smoking aids, the product has alocal rather than systemic effect. Fr. Demande 2,386,307 (Michalon) discloses a dentrifice with the property of dissuading a smoker from smoking tobacco. The toothpaste contains silver nitrate as the active ingredient to generate a physiological distaste for tobacco smoking.

The present invention provides an aid to breaking the smoking habit, which does not requiring brushing teeth, etc. nor contains any of the foregoing disadvantages.

SUMMARY OF THE INVENTION

The invention comprises a mouthwash solution which comprises stabilized silver nitrate in aqueous solution which also helps sore throat and mouth ulcers.

DETAILED DESCRIPTION OF THE INVENTION

Silver nitrate's presence in the oral cavity will cause a bitter taste in the mouth only if there is tobacco smoke present in the mouth. In the absence of tobacco smoke there will be no bitter taste at all.

The main obstacle to the use of a silver nitrate mouthwash as an aid to breaking the smoking habit has been the fact that the silver nitrate is difficult to maintain in aqueous solution and will precipitate from the solution after standing only a few days. The mouthwash of the present invention has a shelf life of at least five months under ambient conditions of temperature, thus rendering the mouthwash commercially useful.

The silver nitrate is used in the compositions of the invention in a smoke aversion proportion. Generally a smoke aversion proportion is one within the range of from 1:1000 to 1:10000 solution concentration.

The silver nitrate is kept in solution through the combined use of three procedures. The first is to use distilled water free of ions. The impurities usually found in tap water precipitate small concentrations of silver from solution.

The second procedure is the addition of 0.001 to 0.005% of nitric acid to the solution. The nitric acid will retard the precipitation of the silver and is a stabilizer.

The third procedure is to package the composition of the invention in a container which is opaque to light. Light will cause silver to precipitate from the solution.

The silver nitrate antismoking mouthwash of the invention is very safe. All of the ingredients (in the concentrations employed) are safe topically or if swallowed (in normal use only negligible amounts are swallowed).

In addition to water, silver nitrate and nitric acid, the compositions of the invention may also contain a wide variety of ingredients conventionally found in mouthwash formulations. Representative of additional ingredients are antiseptics such as cetylpyridinium chloride and domiphen bromide, preservatives, sweetners, and like flavorants, coloring agents, alcohols and the like.

The compositions of the invention may be used by topical application to the mucosa of the oral cavity, at least five times a day for a minimum of two weeks. The preferred method of use for optimum results is as follows.

For best results gargle after every meal and after drinking liquids. First gargle immediately when you wake up before you light up a cigarette. Then gargle immediately after every meal or liquids. In the evening gargle not only after dinner, but also again two to four hours after dinner.

During the first week, it is obligatory to light up a cigarette or pipe after every gargling with this mouthwash and to take two to three puffs (inhalations) in order to develop an aversion to smoking. When the cigarette or pipe causes a bad taste in your mouth, put it out.

During the second week, continue gargling five to six times a day like the first week, but try not to smoke at all. Do not keep any cigarettes with you or at home. It is very important that you do not stop, interrupt or decrease the gargling for the entire two weeks.

Gargling longer than two weeks is not recommended. Before you use the mouthwash again, discontinue it for two weeks. After a two week interval, again follow the above directions for use.

The following example sets forth the manner and the use of the invention and sets forth the best mode contemplated by the inventor for carrying out the invention.

EXAMPLE

The following ingredients are mixed together and bottled in brown glass bottles:

|  | Weight Percent |
|---|---|
| alcohol (ethanol) | 9.25% |
| glycerine | 5.0% |
| sodium saccharine | 0.025% |
| silver nitrate | 0.08% |
| nitric acid | 0.004% |
| cetylpyridinium chloride | 0.003% |
| domiphen bromide | 0.003% |
| mint flavor with benzoic acid and food dyes for sufficient coloring distilled water qs. to | |

| | Weight Percent |
|---|---|
| 1000 ml. | |

The mouthwash is stable for at least 5 months retained in the brown bottles and stored at ambient temperatures (circa 26° C.).

When used in accordance with the above-described directions, human smokers (about one-half) develop aversion to smoking and are able to resist the smoking habit.

What is claimed is:

1. A shelf-stable aid for reducing the smoking habit, which comprises;
    a distilled water solution of silver nitrate having a concentration within the range of from 1:1000 to 1:10000, stabilized with the presence of 0.001 to 0.005 weight percent of nitric acid, said aid being protected from exposure to light.

2. A method of aiding in the reduction the tobacco smoking habit in a human afflicted with said habit, which comprises:
    providing a distilled water solution of silver nitrate having a concentration within the range of from 1:1000 to 1:10000, stabilized by the presence of 0.001 to 0.005 weight percent of nitric acid;
    applying said solution topically to the mucosa of the oral cavity of said human, five times a day, for a period of two weeks; and
    introducing tabacco smoke into the oral cavity following each of the five applications, for the first week of said two week period.

3. The aid of claim 1 wherein the solution additionally comprises an antiseptic.

4. The aid of claim 1 wherein the solution additionally comprises a flavorant.

5. The aid of claim 1 wherein protection from light is rendered by containment of the solution in a brown glass bottle.

6. The method of claim 2 wherein applying is by gargle.

7. The method of claim 2 wherein applying is preceded by a meal or drinking a liquid.

8. The method of claim 2 wherein introducing smoke comprises two to three inhalations of a cigarette or pipe smoke.

9. A composition, which comprises; by weight
    9.25 percent of ethanol;
    5.0 percent of glycerine;
    0.025 percent of sodium saccharine;
    0.08 percent of silver nitrate;
    0.004 percent of nitric acid;
    0.003 percent of cetylpyridinium chloride;
    0.003 percent of domiphen bromide; and sufficient distilled water to make up to 1000 ml.

* * * * *